United States Patent [19]

Carman, Jr. et al.

[11] Patent Number: 5,850,623
[45] Date of Patent: Dec. 15, 1998

[54] METHOD FOR STANDARDIZING RAMAN SPECTROMETERS TO OBTAIN STABLE AND TRANSFERABLE CALIBRATIONS

[75] Inventors: Howard Smith Carman, Jr., Blountville; Daniel Charles Alsmeyer, Kingsport; Carlos Humberto Juarez-Garcia, Kingsport; Aaron Wayne Garrett, Kingsport; Bruce Edwin Wilson, Kingsport; Vincent Alvin Nicely, Kingsport, all of Tenn.

[73] Assignee: Eastman Chemical Company, Kingsport, Tenn.

[21] Appl. No.: 947,689

[22] Filed: Oct. 9, 1997

Related U.S. Application Data

[60] Provisional application No. 60/043,588 Mar. 14, 1997.

[51] Int. Cl.⁶ .............................. G01J 3/44; G01N 21/65; G01N 33/00
[52] U.S. Cl. .............................. 702/28; 702/23; 702/27; 702/30; 702/85; 702/90; 702/172; 356/301; 356/346; 250/252.1; 250/339.07; 250/339.09; 250/339.06
[58] Field of Search ..................... 702/22, 27, 28–30, 702/32, 23, 76, 77, 85, 87–91, 97, 172, 156, 155; 356/301, 346; 250/339.06–339.07, 339.09, 339.11, 339.12, 252.1; 364/724.12, 728.01

[56] References Cited

U.S. PATENT DOCUMENTS

| | | |
|---|---|---|
| 4,866,644 | 9/1989 | Shenk et al. . |
| 5,243,546 | 9/1993 | Maggard . |
| 5,303,165 | 4/1994 | Ganz et al. . |
| 5,357,336 | 10/1994 | Ruhl et al. . |
| 5,455,673 | 10/1995 | Alsmeyer et al. . |
| 5,459,677 | 10/1995 | Kowalski et al. . |
| 5,498,875 | 3/1996 | Obremski et al. ............ 250/458.1 |
| 5,545,895 | 8/1996 | Wright et al. ................... 250/282 |
| 5,559,728 | 9/1996 | Kowalski et al. ............... 702/85 |
| 5,610,836 | 3/1997 | Alsmeyer et al. . |
| 5,638,172 | 6/1997 | Alsmeyer et al. . |
| 5,652,653 | 7/1997 | Alsmeyer et al. ............ 356/301 |
| 5,657,404 | 8/1997 | Buchanan et al. ............. 385/12 |
| 5,710,713 | 1/1998 | Wright et al. ................. 702/23 |

FOREIGN PATENT DOCUMENTS

WO 96/24832  10/1994  European Pat. Off. .

OTHER PUBLICATIONS

Brownrigg, J. T. "Wavelength Calibration Methods for Low–Resolution Photodiode Array Spectrometers," *Appl. Spectrosc.*, 47:1007–1014 (1993).

Blanco et al., "Wavelength Calibration Transfer Between Diode Array UV–Visible Spectrophotometers," *Appl. Spectrosc.*, 49:593–597 (1995).

(List continued on next page.)

*Primary Examiner*—James P. Trammell
*Assistant Examiner*—Tuan Q. Dam
*Attorney, Agent, or Firm*—Jaeckle Fleischmann & Mugel, LLP

[57] ABSTRACT

A method for providing a standard Raman spectrum from a sample uses a particular Raman spectrometry apparatus or any similar Raman spectrometry apparatus, which is used to simultaneously irradiate a reference material and at least one sample, thereby obtaining their respective convolved Raman spectra. Using a defined standard energy dispersion characteristic and a standard Raman spectrum of the reference material, a convolution function is determined and applied to produce a deconvolved Raman spectrum of the sample. This deconvolved spectrum is multiplied by a defined standard photometric response function to produce a standard Raman spectrum of the sample. A method for providing an accurate and precise quantitative analysis of the chemical composition and/or physical properties of an unknown sample uses the standard Raman spectra of a plurality of known samples to construct a normalized calibration, which is applied to a standard Raman spectrum of the unknown sample to produce an accurate and precise quantitative analysis thereof, using any similar Raman spectrometry apparatus.

49 Claims, 1 Drawing Sheet

OTHER PUBLICATIONS

Carter et al., "Frequency/Wavelength Calibration of Multipurpose Multichannel Raman Spectrometers. Part I: Instrumental Factors Affecting Precisions," *Appl. Spectrosc.,* 49:1550–1560 (1995).

Carter et al., "Frequency/Wavelength Calibration of Multipurpose Multichannel Raman Spectrometers. Part II: Calibration fit Considerations and Calibration Standards," *Appl. Spectros.,* 49:1561–1576 (1995).

Cho et al., "Wavelength Calibration Method for a CCD Detector and Multichannel Fiber–Optic Probes," *Appl. Spectrosc.,* 49:1841–1845 (1995).

Press et al., "Numerical Recipes: The Art of Scientific Computing," *Cambridge University Press,* 86–89, 381–383, 407–412 (1989).

Fig. 1

METHOD FOR STANDARDIZING RAMAN SPECTROMETERS TO OBTAIN STABLE AND TRANSFERABLE CALIBRATIONS

CROSS-REFERENCE TO RELATED APPLICATIONS

This application claims priority from Provisional Application Ser. No. 60/043,588, METHOD FOR STANDARDIZING RAMAN SPECTROMETERS TO OBTAIN STABLE AND TRANSFERABLE CALIBRATIONS, filed Mar. 14, 1997 by Alsmeyer et al.

FIELD OF THE INVENTION

This invention relates to calibration and standardization of Raman spectrometers and, more particularly, to a method for standardizing Raman spectrometers such that stable, transferable calibrations relating spectral responses to quantitative analyses of samples or processes can be generated, using any one of a plurality of similar Raman spectrometers that may be subject to varying instrumental or environmental conditions.

BACKGROUND OF THE INVENTION

Calibration refers to the process of using empirical data and prior knowledge to determine how to estimate quantitative analyses from new measurements. Many analytical instruments provide a response that does not directly relate to the desired analytical measurements. For example, a chromatogram may provide a series of peaks that relate to the amounts of components injected for analysis. However, each component may have different response factors that would bias the analysis unless a calibration is performed to determine the individual component response factors.

Similarly, spectroscopic measurements such as near-infrared spectroscopy (NIRS) and Raman spectroscopy provide vibrational spectra that relate to the molecular motions of individual components. Each component has distinct vibrational motions and each vibrational motion has a certain response factor dependent upon the characteristics of the molecule. The response factors affect the relative intensities of each vibrational band such that direct measures of vibrational intensities will not directly yield accurate compositional information. Calibration provides the means by which the relative response factors are accounted for in the transformation of the vibrational spectrum to the quantitative compositional information.

Raman spectroscopy measures the inelastic scattering of incident radiation from a sample and compares the scattered radiation to the incident radiation to provide an energy loss (Stokes) or energy gain (anti-Stokes) spectrum that relates to the vibrational motions of sampled molecules. The obtained Raman spectra can be related to the desired quantitative analyses. Raman spectroscopy can provide rapid and precise multivariate signal responses at a plurality of wavelengths for on-line or in situ process environments. An overview of analytical Raman spectroscopy is provided in J. G. Grasselli and B. J. Bulkin, editors, *Analytical Raman Spectroscopy*, 1991, John Wiley & Sons, New York.

In their most powerful applications, both NIRS and Raman spectroscopy require the development of calibrations that correlate acquired multivariate signal responses to quantitative analytical measurements obtained by some reference analytical method, for example, nuclear magnetic resonance spectroscopy (NMR), gas chromatography, or gravimetric analysis. Various approaches for developing calibrations have been described in, for example, H. Martens and T. Naes, *Multivariate Calibration*, 1989, John Wiley & Sons, New York, and include such methods as multiple linear regression (MLR), principal component regression (PCR), and partial least squares regression (PLS), among others. The general problem of constructing a calibration lies in determining the relationships between a set of multivariate signal responses, X, and a set of quantitative measurements, Y, such that new measurements of the multivariate signal responses for an unknown sample can be transformed to yield accurate quantities of the components of the unknown sample. Typically, multivariate signal responses, X, and quantitative measurements, Y, are obtained for a number of known samples that contain all the expected variations in composition and physical state that correlate with the analytical measurements of the unknown samples. Development of a calibration is therefore time-consuming, expensive, and tedious.

Once a calibration is generated, there are a number of situations that could cause it to become inaccurate. For example, an instrument component could fail catastrophically, requiring replacement; the replacement component may differ from the original component, causing a change in the measured multivariate signal responses and thereby introducing a shift or bias in the quantitative analyses obtained with the original calibration. Similarly, instrument components can change in character as they age or as they are exposed to various environmental conditions, for example, changing temperature and humidity. Any drift or change that affects the measured signal response can create a drift or change in the quantitative predictions of the calibration. Furthermore, a calibration generated using signal responses measured with one instrument may not be accurate when applied to signal responses measured with another instrument because of differences in response functions between the two instruments.

Clearly, it would be highly desirable to find a way of obtaining a stable calibration that could be transferred from one instrument to another and still provide accurate quantitative predictions. Such a calibration would be particularly useful when applied to quantitative analyses of manufacturing processes. If the calibration as developed could be reliably transferred between different instruments subject to varying environmental conditions, it could be applied to multiple instruments at various manufacturing sites and thus make it possible to attain more uniform quality among processes and products.

Standardization is here defined as the process of using empirical data and prior knowledge to determine how to generate and maintain a calibration such that quantitative analyses derived from new measurements of a given sample or process are equal, within prescribed error limits, to quantitative analyses derived from previous measurements of an identical sample or process using the same or different instruments. Various approaches to instrument standardization are described in O. E. DeNoord, "Multivariate Calibration Standardization" in *Chemom. Intell. Lab. Syst.*, 1994, vol. 25, pp 85–97, and in E. Bouveresse and D. L. Massart, "Standardisation of Near-Infrared Spectrometric Instruments: A Review" in *Vib. Spect.*, 1996, vol. 11, pp 3–15, the disclosures of which are incorporated herein by reference.

In one standardization strategy particularly relevant to the present invention, measurement data acquired under new conditions, e.g., with a different instrument, at a different temperature, or at a later time, are transformed such that they become equivalent to data that would have been acquired under the original conditions for which a calibration was built. In this approach, a calibration is developed for one instrument (a reference instrument), and data measured on a second instrument (a target instrument) are transformed to appear as though they were measured on the reference instrument. The required transformations are determined from comparisons of spectra for "transfer samples," which are samples with known properties and compositions that are measured on both the reference and target instruments. Differences between spectra obtained for transfer samples on the two instruments are used to produce correlations that can transform a spectrum measured on the target instrument to appear as though it were measured on the reference instrument.

Shenk et al, U.S. Pat. No. 4,866,644, the disclosure of which is incorporated herein by reference, describes a method where a series of standard samples (typically 30 samples) are measured on both a reference instrument and a target instrument. Statistical correlation techniques are used to determine correction factors that, when applied to data for an unknown sample from the target instrument, provide output that is substantially the same as would be obtained if the unknown test sample were measured with the reference instrument.

Maggard, U.S. Pat. No. 5,243,546, the disclosure of which is incorporated herein by reference, describes a method for standardizing a target instrument to a reference instrument, whereby the number of transfer samples measured on the target instrument may be significantly smaller than the number required to originally calibrate the reference instrument.

Kowalski et al., U.S. Pat. No. 5,459,677), the disclosure of which is incorporated herein by reference, describes several approaches for transferring a multivariate calibration from a reference instrument to a target instrument that use a variety of methods for establishing a correlation between data obtained for transfer samples measured on both instruments.

The methods described in the aforementioned three references rely on a reference instrument being used to build the original calibration. If the original reference instrument were to become disabled, a new calibration would have to be generated on a new reference instrument.

Villemoes et al., PCT International Application WO 96/24832, the disclosure of which is incorporated herein by reference, describes a method where a spectrum (or some part thereof) of at least one standard sample is chosen to be a "standard response." Measurements of the same standard sample(s) on any target instrument are compared with the previously defined standard response to determine parameters that, when applied to measurements of an unknown sample, generate a spectrum substantially identical to one generated in the spectrometer used to define the standard response. However, the actual spectrometer used to generate the standard response does not need to be maintained as a reference instrument.

A disadvantage of the above described standardization methods is their dependence on measurements of transfer samples of known and stable composition. The transfer samples must be very stable so that any differences between data measured under the new conditions and data measured under the original conditions relate only to changes in the measurement conditions and not to changes in the samples. In many cases, transfer samples are not sufficiently stable to be maintained for long periods of time; it is then necessary to employ as transfer samples prepared mixtures of components with specified concentrations. It is improbable that such mixtures can be prepared repeatedly with exactly the same component quantities. Furthermore, methods that rely on measurements of transfer samples are not well suited for instruments used for analysis in industrial processes. Industrial process instruments are often located in surroundings of widely varying environmental conditions such as, for example, temperature and humidity. The spectroscopic characteristics of a transfer sample may vary with environmental conditions, particularly temperature, due to chemical and/or physical effects such as, for example, hydrogen bonding, degradation, evaporation, etc., that are strongly temperature dependent. Spectroscopic changes induced in the transfer sample by environmental conditions may be independent of variabilities in the instrument response or in the process being analyzed, resulting in calibration errors that are introduced by the standardization process itself.

Standardization methods that do not require the measurements of chemical standardization samples have been described in Ruhl et al., U.S. Pat. No. 5,357,336, and Ganz et al., U.S. Pat. No. 5,303,165, the disclosures of which are incorporated herein by reference. These methods rely upon spectral measurements of a Fabry-Perot etalon as a standard reference material. Spectra measured for the etalon are used to determine wavelength and intensity calibration parameters that are subsequently used to standardize each measured sample spectrum to appear as though it were measured with the same wavelength and intensity parameters as were present when the original calibration was built.

Although applicable in principle to many types of spectrometric analysis, the methods described in these latter two references are best suited for absorption measurements, where the intensity of radiation from the instrument source is measured after passing through the sample. The relatively intense radiation from the instrument source passes through the etalon, and the modulation of the light intensity created by the etalon has a sufficient magnitude to ensure accurate and precise determination of the positions and intensities of maxima and minima in the resulting interference spectrum. These methods are not well suited for Raman spectroscopy, where the measured radiation intensities are extremely weak compared to absorption measurements, and for which there is no throughput of light when there is no Raman scattering by the sample.

A method for standardizing a Raman spectrometer to compensate for several possible apparatus variabilities is described by Alsmeyer et al., U.S. Pat. Nos. 5,455,673, 5,638,172, and 5,652,653, the disclosures of which are incorporated herein by reference. The method provides "dynamic standardization" that entails simultaneous measurement of spectra for a sample material and a reference material. A convolution function of the two spectra is determined, which can be applied to the sample data to produce a standard Raman spectrum of the sample that has been compensated for variabilities in the instrument response. Although the method described in U.S. Pat. Nos. 5,455,673, 5,638,172, and 5,652,653 is very successful in compensating for instrument variabilities and providing short-term standardization of a single Raman instrument, it does not provide a means for compensating for instrument-to-instrument variabilities or for long-term drifts or changes in the instrument response function. The method therefore does not provide for generation of a robust calibration that can be transferred to a plurality of instruments and is stable over long periods of time.

The previously known standardization methods described above are all viable in certain situations, but they do not provide the completeness, robustness, and reliability desired for standardizing analytical Raman spectrometers in an industrial process environment.

In many cases, factors other than instrumental variabilities can affect measured spectra in a way that causes a calibration to become inaccurate. For example, in molten or liquid process streams, interfering effects such as bubbles, particulates, and turbidity can alter the overall intensity of the scattered radiation in an unpredictable fashion. Similarly, for solid samples, the sample shape, uniformity, and thickness can effect the overall intensity of the observed signal. When Raman spectra are obtained in a multiplexed fashion, i.e., the signal responses at all wavelengths are measured simultaneously, the effect of such interferences is to multiply an entire spectrum by an unknown constant that is unique to that individually collected spectrum. Spectral responses that have been multiplied by an unknown random number are not suitable for calibration directly using the usual multivariate statistical approaches that are known in the art.

A solution to the problem of building calibration techniques using spectra that are not normalized to the same intensity scales has been described in Alsmeyer et al., U.S. Pat. No. 5,610,836, the disclosure of which is incorporated herein by reference. In this method, a set of multivariate signal responses such as spectra, represented by a matrix X, are obtained for a set of calibration samples having a set of known quantities, represented by a matrix Y. The matrix X may represent spectra that are not normalized to the same intensity scales due to interfering factors, as described above. The X and Y matrices are employed to calculate a set of normalization multipliers that, when applied to the matrix X, generates a set of multivariate signal responses that have been normalized to the same intensity scales. This normalized set of signal responses is then used to generate a calibration that provides accurate analysis of a sample of unknown constitution by a particular analytical apparatus. The method described in U.S. Pat. No. 5,610,836, while it does compensate for certain variabilities in the processes or samples being analyzed, does not provide compensation for variability in the apparatus.

PROBLEM TO BE SOLVED BY THE INVENTION

The ability to perform on-line or in situ quantitative analyses of industrial manufacturing processes can substantially improve the quality, efficiency, and safety of the processes by providing real-time analytical data that can be used to monitor chemical reaction process streams and thereby control the processes. Samples from process streams that can be usefully examined in accordance with the present invention include a variety of polymeric compositions, including, for example, cellulosic compositions and polymeric materials such as polyesters or polyolefins that are produced by the reaction of lower molecular weight reactant compounds. Samples to be analyzed by the method of the invention can also comprise material contained in a distillation process as well as material situated in a living organism.

Raman spectroscopy is thus capable of providing rapid and precise multivariate signal responses for on-line or in situ quantitative analyses of a great variety of materials. In order to achieve reliable quantitative analyses of these materials, it is highly desirable to establish robust and reliable calibrations for any of a number of Raman spectrometers that do not drift or change because of instrumental variabilities and can be transferred reliably from one Raman apparatus to another. The present invention provides a standardization method for Raman spectrometers that enables this goal to be achieved. The resulting calibrations also allow the accurate and precise quantitative analysis of a wide variety of samples of unknown composition.

SUMMARY OF THE INVENTION

In accordance with the present invention is a method for producing a standard Raman spectrum from a sample using a particular Raman spectrometry apparatus or any similar Raman apparatus comprising a substantially monochromatic radiation source, excitation optical means, reference optical collection means, at least one sample optical collection means, a spectrograph, and a multi-channel array detector.

A reference material and at least one sample are irradiated using the Raman spectrometry apparatus, and convolved Raman spectra of the reference material and the sample are simultaneously acquired, using a reference channel and a sample channel, respectively, of the multi-channel array detector. Noise spikes are optionally identified and removed from the convolved spectra of the reference material and the sample to produced despiked convolved spectra.

Using a second radiation source, each optical collection means and the spectrograph is irradiated, and the resulting signals are detected by the detector, producing a photometric reference spectrum for each optical collection means. Each of the optionally despiked convolved Raman spectra of the reference material and the sample is divided by the corresponding photometric reference spectrum to produce compensated convolved Raman spectra of the reference material and sample.

Using a third radiation source, the spectrograph is irradiated, and the resulting signals are detected in each channel of the detector, producing a third radiation source spectrum for each detector channel. From the third radiation source spectrum for each channel and a defined standard energy dispersion characteristic is constructed a corresponding wavelength/energy correlating equation for each detector channel. Each of these equations is applied to each corresponding compensated convolved Raman spectrum of the reference material and the sample, to produce linearized convolved Raman spectra of the reference material and sample. The spectrum of the reference material so obtained can be optionally corrected to remove background signals.

A convolution function is determined from a defined standard Raman spectrum of the reference material and the optionally corrected linearized convolved Raman spectrum of the reference material. The convolution function is applied to adjust the linearized convolved Raman spectrum of the sample, thereby producing a deconvolved Raman spectrum of the sample. The deconvolved Raman spectrum of the sample is multiplied by a defined standard photometric response function to produce a standard Raman spectrum of the sample not only from a particular Raman spectrometry apparatus but from any similar Raman apparatus.

Further in accordance with the present invention is a method for providing an accurate and precise quantitative analysis of the chemical composition and/or physical properties of an unknown sample by generating a standardized calibration that can be applied to a particular, or any similar, Raman spectrometry apparatus.

Using a plurality of samples of known chemical composition and/or physical properties and the Raman spectrometry apparatus, a set of multivariate signal responses comprising standard Raman spectra of the samples is produced. From the set of multivariate signal responses and the known chemical composition and/or physical properties of the samples, a normalized calibration is constructed. The normalized calibration is applied to a standard Raman spectrum obtained from a sample of unknown chemical composition and.or physical properties to provide an accurate and precise quantitative analysis of the unknown sample.

DETAILED DESCRIPTION OF THE INVENTION

The present invention is a method for standardizing a Raman spectrometer such that a robust and stable calibration relating Raman spectral responses to quantitative analyses of samples or processes can be generated, maintained, and transferred to any number of similar spectrometers. This standardization method requires:

defining a desired spectrometer standard state that specifies the energy dispersion characteristics and photometric response characteristics desired for a spectrometer in a given application;

transforming measured spectra into "standard spectra" having the same energy dispersion and photometric response characteristics as those defined for the spectrometer standard state, the functions required to carry out these transformations being derived from measurements of standard reference materials having well known spectroscopic properties;

using standard spectra, building a normalized multivariate calibration that compensates for multiplicative intensity differences among the standard spectra; and applying the normalized calibration to predict quantitative analyses from standard spectra obtained in subsequent measurements.

In contrast to methods known in the art, the spectrometer standard state as defined in the present invention is not derived from measurements or spectra obtained from any particular "reference" spectrometer but rather is a construct that defines the characteristics desired for a spectrometer in a given application. In contrast to methods known in the art, the standard materials employed to derive the transformation functions are not "transfer" standards in that they are not related in chemical composition to the samples or process for which the calibration is being generated.

Individual processes known in the art to transform measured spectra into standard spectra and to generate a normalized multivariate calibration are incapable of providing the level of standardization required for a process Raman spectrometer. The method of the present invention constitutes a new and unobvious combination of known individual processes to construct a stable calibration that can be transferred from one Raman spectrometer to any of a plurality of similar instruments, including those used for industrial process analyses.

The method of the present invention is applicable to Raman spectrometers for which a reference spectrum and a spectrum of the sample to be analyzed are acquired simultaneously, as described in the previously discussed U.S. Pat. No. 5,455,673. The reference spectrum may be a suitable fragment of the sample spectrum that remains unchanged as the sample changes composition, temperature, etc. In general, however, it is rare that a sample will exhibit a suitable spectral fragment that can be used as a reference spectrum. In a more preferred embodiment, the process is applied to multichannel spectrometers that use a laser as a source of monochromatic excitation radiation, a grating spectrograph for wavelength (or energy) dispersion, and an array detector such as,for example, a charge-coupled device (CCD) detector. The laser source simultaneously irradiates both a reference material and one or more samples to be analyzed, and the Raman spectral responses of the reference material and the sample(s) are acquired simultaneously using a different set of detector elements,or pixels, to detect radiation from the reference material and from each sample.

Since each set of pixels effectively acts as a different detector, and radiation from each process or sample is collected and transmitted to the detector by different optical elements, for example, different filters or optical fibers, each sample or process is essentially measured with a different instrument. Reference to different spectrometers herein therefore also pertains to different channels of a multichannel spectrometer.

Figure 1:
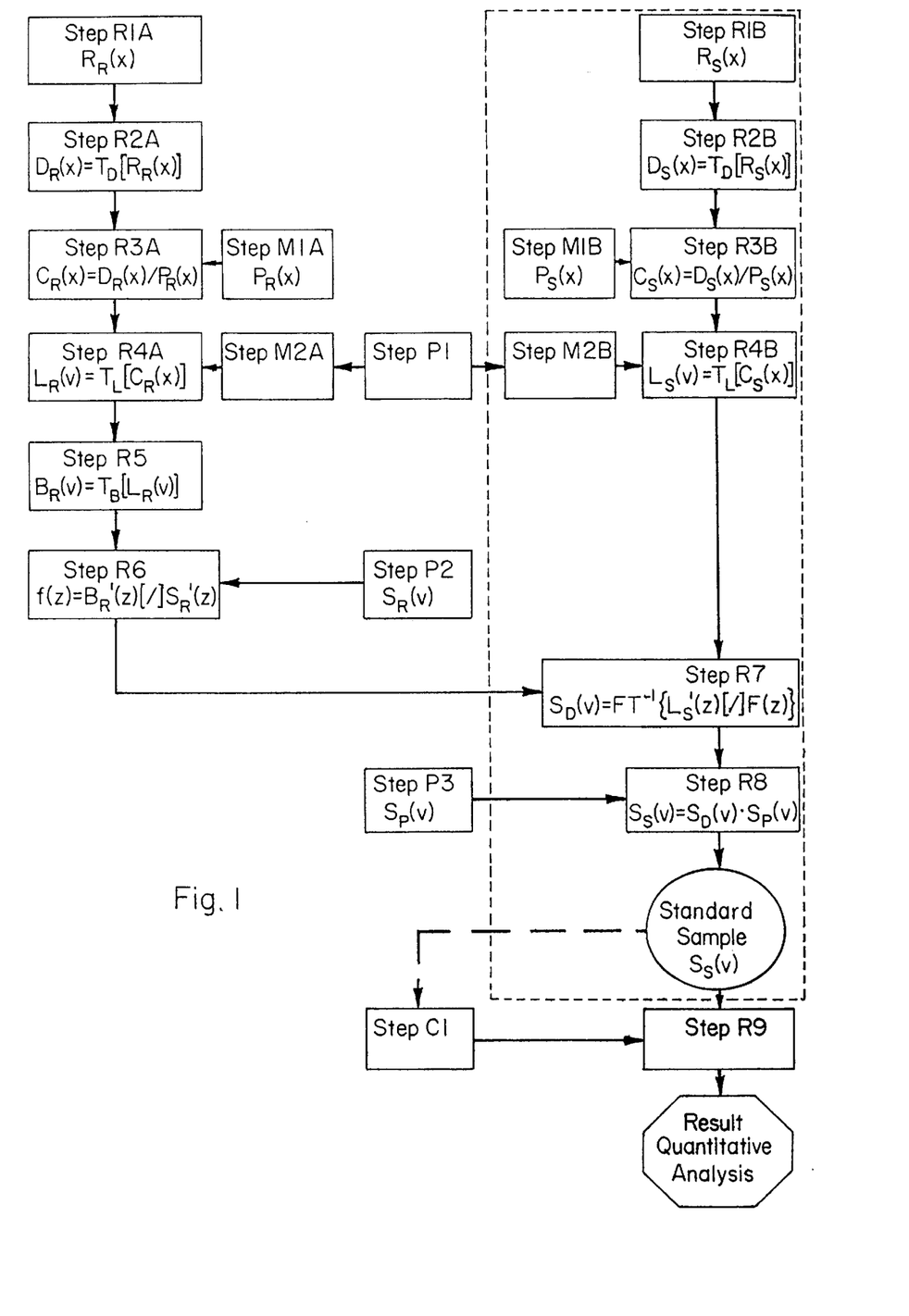
FIG. 1 is a schematic diagram of the method of the invention for standardizing Raman spectrometers and obtaining stable, transferable calibrations.

A schematic diagram of the method of the present invention is shown in FIG. 1 for the case of one sample being analyzed. In the situation where multiple samples are being analyzed simultaneously, the steps shown within the dotted outline are performed for each channel of the spectrometer used to acquire sample spectra.

Standardized Universal Raman Environment (SURE)

The multivariate Raman signal responses measured for a given sample or process depend upon not only the sample or process measured but also upon many instrumental factors, including: (1) the dispersion characteristics of the spectrometer, (2) the energy of the excitation source radiation, (3) the number of detector pixel elements that are illuminated by the dispersed radiation and for which intensity signals are measured, (4) the quantum efficiency, or sensitivity, of each detector pixel at different wavelengths, and (5) the throughput, i.e., transmission characteristics, of the collection optics (probe, fibers, filters, spectrometer, etc.). All of these factors can vary from instrument to instrument and/or from measurement to measurement. However the Raman-shift energies and spectral intensities of vibrational features most important for quantitative analysis are determined by the spectroscopic characteristics of the samples being analyzed, not by the instrument used for analysis. Therefore the present standardization method requires determination of the energy region important to the application of interest, specification of the energy resolution needed to achieve the desired analysis, and definition of an "ideal" intensity response function. These factors are then used to define functions that describe the energy dispersion characteristics and intensity response function desired for a spectrometer for the given application. The functions so defined do not depend upon the characteristics of any particular spectrometer but rather characterize the state of a spectrometer having the characteristics desired for a given application. A spectrometer so characterized provides a standard state into which measurements from actual spectrometers are to be transformed. This defined standard state is referred to herein as the Standardized Universal Raman Environment (SURE).

Characterization of the SURE requires the definition of three parameters that establish the energies and relative intensity scales of each point in a spectrum:

(a) a standard energy dispersion characteristic, (b) a standard spectrum of the reference material, and (c) a standard photometric response function.

These parameters are discussed in the sections that follow.

(a) Standard energy dispersion characteristic

Step P1 in FIG. 1 defines the standard energy dispersion characteristic for the SURE, which specifies the number of data points to be included in each standard spectrum and the energy spacing between data points. In a preferred embodiment, the energy dispersion characteristic of the SURE is chosen to be linear in energy, i.e., the energy spacing between adjacent points in the spectrum is constant. A linear energy dispersion basis facilitates the process of dynamic standardization, which is described below.

It may be established, for example, that the Raman-shift energy region of importance for a given application lies between 500 cm$^{-1}$ and 2000 cm$^{-1}$ and that an energy spacing between points of 3 cm$^{-1}$ is desired. The energy dispersion basis would then be defined such that each spectrum would comprise 501 points (i=0–500), equally spaced by 3 cm$^{-1}$. Once the number of points and the energy spacing between points is defined, each point is assigned a specific energy value. The choice of specific energy value is arbitrary, however, and serves only as a number used to facilitate calculations carried out in the linearization and dynamic standardization processes, which will be described below. For convenience, the specific energy values are chosen to be approximately equal to those expected for the actual measurement. Thus, for the example above, an energy scale could be established such that the first point (i=0) corresponds to a Raman-shift energy of 500 cm$^{-1}$ and each other point corresponds to a Raman-shift energy of $(3i+500)$ cm$^{-1}$. If preferred, the energy scale may be established in units of total radiation energy rather than Raman-shift energy. For example, if an excitation source with a nominal wavelength of 800 nm, corresponding to a radiation energy of 12,500 cm$^{-1}$, were used for measurements in the above example, the absolute energies of each point would have assigned values of $(12,000-3i)$ cm$^{-1}$. The choice of absolute energy scale is arbitrary, however, and need not necessary correlate with the absolute energies actually measured.

Spectrometers to be used for measurements must be configured such that the range of energies actually measured is equal to or greater than those defined for the SURE. Once defined, the energy dispersion characteristic, i.e., the number of points per spectrum and the energies corresponding to each point, is stored in digital form for future use in the linearization process, to be described subsequently.

(b) Standard spectrum of the reference material

Step P2 in FIG. 1 defines a standard reference spectrum, $S_R(v)$, for the SURE. The standard reference spectrum should be a true representation of the underlying shape of a measured spectrum of the standard reference material. The choice of reference material is arbitrary, but it should be a material that provides a consistent and reliable Raman spectral response. For example, diamond is a preferred reference material because it is chemically and physically stable and its Raman spectrum is simple, comprising a single peak with a Raman-shift energy of 1332 cm$^{-1}$.

The standard reference spectrum may be a theoretical representation of the invariant portion of a measured reference spectrum (e.g., a gaussian or lorentzian distribution function that closely matches the peak shape of a measured reference spectrum); it may also be a previously measured reference spectrum that has been adjusted or smoothed. Preferably, the standard reference spectrum is obtained by averaging several measured reference spectra and transforming the average spectrum into a linear energy dispersion basis using the linearization process, which will be described later. Once defined, the standard reference spectrum is stored in digital form, to be used in the dynamic standardization process, also to be described later.

(c) Standard photometric response function

The radiation intensity measured at each detector pixel is a function of the radiation intensity produced by Raman scattering at the sample and the efficiency with which that radiation is collected, dispersed, and detected. A measured Raman spectrum is therefore a convolution of the true sample spectrum with some instrumental response function. The function describing the overall efficiency for collecting and detecting radiation at each wavelength or energy is referred to herein as the photometric response function. This function depends on the throughput, or transmission efficiency, of each optical component, i.e., probes, fibers, filters, etc., used to collect and transmit scattered radiation to the detector and on the efficiency of each detector pixel, which generally varies with wavelength or energy. Because of variabilities in optical components and detectors, the photometric response function will vary from instrument to instrument. Likewise, any changes in the components of a given instrument can create changes in the photometric response function and therefore changes in measured spectra.

Step P3 in FIG. 1 defines the standard photometric response function for the SURE. Although the photometric response function of a given spectrometer will depend upon the specific characteristics of its components, the choice of the standard photometric response function for the SURE is arbitrary. It may be defined as equal to the photometric response function measured for a given spectrometer or, alternatively, as the average of a plurality of photometric response functions measured for several different spectrometers. In some applications, it may be desirable to weight some regions of a spectrum more than others when building a multivariate calibration technique; for such applications, the standard photometric response function may be defined to simulate more efficient detection in some spectral regions than in others. Preferably, and more simply, the standard photometric response function, $S_p$, can be defined so that the overall detection efficiency is independent of energy and therefore equal to unity at all energies:

$S_p(v)=1$ (for all v)

Once defined, the standard photometric response function is stored in digital form to be used in the transformation of measured spectra into the SURE.

The functions chosen to define the SURE are mathematical constructs that describe the state of a spectrometer desired for a particular application. By definition, these functions are independent of the characteristics of any particular spectrometer and they do not drift or change. Once defined and stored in digital form, they may be maintained and transferred to any location and used in other mathematical processes to transform spectra actually measured with any spectrometer into spectra that have the same energy dispersion characteristics and relative intensity characteristics as those defined for the SURE. Spectra that have been so transformed are referred to herein as "standard spectra."

The following individual processes are used to calibrate the energy dispersion and intensity characteristics of a spectrophotometer and to transform measured spectra into standard spectra:

(1) measurement of convolved spectra and removal of cosmic spikes (2) photometric compensation (3) linearization (4) optional background correction of reference spectrum (5) dynamic standardization (6) weighting of standard spectra (7) development of a normalized calibration Each of these processes will be described in sections that follow.

(1) Measurement of Convolved Spectra and Removal of Cosmic Spikes

In step R1A of FIG. 1, a convolved spectrum, $R_R(x)$, is acquired for the reference material, i.e., a spectrum convolved with the response function of the spectrometer used to acquire the spectrum. In step R1B of FIG. 1, a convolved spectrum, $R_S(x)$, is acquired for the sample or process being analyzed. These two steps are performed simultaneously using the same source of excitation radiation to irradiate both the reference material and the sample or process being analyzed.

Noise "spikes" created by cosmic rays and other interferences not related to the true spectral responses of the reference or sample are often observed in measurements from CCD detectors. Methods for detecting and removing these noise spikes are known in the art and have been described, for example, in H. Takeuchi et al., "Simple and Efficient Method to Eliminate Spike Noise From Spectra Recorded on Charge-Couple Device Detectors" in *Appl. Spectrosc.*, 1993, vol. 47, pp129–131, the disclosure of which is incorporated herein by reference.

In steps R2A and R2B of FIG. 1, an appropriate despiking procedure, denoted $T_D[\ ]$, is used to remove noise spikes from the convolved reference spectrum and convolved sample spectrum, respectively, to give "despiked" spectra:

$$D_R(x)=T_D[R_R(x)] \text{ and } D_S(x)=T_D[R_S(x)]$$

(2) Photometric Compensation

Photometric compensation refers herein to a process by which spectra measured on any given spectrometer are compensated for variabilities in the spectrometer's photometric response function. All spectra measured with a given spectrometer are compensated using a spectrum measured for some "photometric standard." The photometric standard should provide a stable, reproducible, and well-characterized radiation spectrum that has substantial intensities at all wavelengths analyzed by the spectrometer and is invariant over a wide range of environmental conditions such as temperature and humidity. Any differences between two spectral measurements of the photometric standard should reflect differences in the photometric response functions of the instrument(s) used to acquire the spectra and not differences in the spectra of the standard.

Photometric standards comprising white-light emission sources have been described in, for example, M. Fryling et al., "Intensity Calibration and Sensitivity Comparisons for CCD/Raman spectrometers" in *Appl. Spectrosc.*, 1993, vol. 47, pp1965–1974, and Y. Wang and R. L. McCreery, "Evaluation of a Diode Laser/Charged Coupled Device Spectrometer for Near-Infrared Spectroscopy" in *Anal. Chem.*, 1989, vol. 61, pp2647–2651, the disclosures of which are incorporated herein by reference. White light emission sources have well characterized spectral profiles and provide broad radiation spectra that can be tuned by adjusting the temperature of the radiator. However, there are disadvantages to using white-light emission sources as photometric standards in an industrial process environment. One disadvantage is that it is often difficult to reproducibly launch the emission radiation into the collection optics of a spectrometer, resulting in substantial variations in the measured spectral profiles. This is especially true in an industrial process environment where it is often difficult to locate the source near the sampling optics of the spectrometer. Furthermore, the spectral profile of a white light source depends strongly upon the temperature of the radiation emitter. In a process environment, the ambient temperature often fluctuates substantially, making it difficult to stabilize the temperature of the white light source.

Photometric standards comprising fluorescent materials with broad, well-characterized fluorescence profiles are described, for example, in H. Hamaguchi, "Calibrating Multichannel Raman Spectrometers" in *Appl. Spec. Rev.*, 1988, vol. 24, pp 137–174, the disclosure of which is incorporated herein by reference. A fluorescent material has the advantage that it can be easily transported to the sampling optics, and the material can be irradiated by the same laser source as is used in the Raman analysis, provided that the laser has sufficient energy to excite fluorescence in the material. A disadvantage of many fluorescent materials is that they are often not stable for extended periods of time, especially when irradiated with intense laser radiation. Furthermore, there are few known materials that fluoresce when excited with near-infrared radiation (800–1000 nm), a region of importance for industrial process Raman spectroscopy.

For Raman applications using near-infrared excitation radiation, a preferred embodiment of the present invention utilizes a fluorescent photometric standard comprising a silicate glass doped with metal oxides. Doped glasses of this type are described in, for example, E.J. Sharp et al., "Chromium-Ytterbium Energy Transfer in Silicate Glass" in *J. Appl. Phys.*, 1973, vol. 44, p 4098, the disclosure of which is incorporated herein by reference. Fluorescence can be generated by near-infrared excitation of these materials, and their fluorescence spectra are not substantially affected by factors such as laser power, length of irradiation, or ambient temperature or humidity. In this embodiment, radiation from the excitation source of the spectrometer is transmitted to the doped glass standard with the same optics used to transmit source radiation to the reference or sample during normal operation of the spectrometer; fluorescence radiation from the standard is then collected and detected with the same collection optics and detector channels as used in the normal operation of the spectrometer.

The spectral response of an appropriate photometric standard is measured in steps M1A and M2A of FIG. 1, yielding photometric standard spectra $P_R(x)$ and $P_S(x)$ for, respectively, the reference and sample channels. This is accomplished by illuminating the whole of the collection optics, from the sampling point to the detector, of each channel with the radiation emitted by the photometric standard, thereby acquiring the spectra.

The photometric response of a spectrometer is not expected to change substantially unless an optical component substantially changes or is replaced, a major repositioning of components occurs, or a substantial change in environmental conditions takes place. Therefore, photometric standard spectra need to be acquired only occasionally, for example, during initial instrument set-up, after component replacement or spectrometer maintenance, or as a periodic check, as dictated by the accuracy of analysis required for a given application. Once acquired, the photometric standard spectrum for each channel is stored in digital form and used to compensate every spectrum acquired with that channel of the spectrometer during normal operation.

In step R3A of FIG. 1, the despiked reference spectrum, $D_R(x)$, is divided by the photometric standard spectrum measured on the reference channel to give a photometrically compensated reference spectrum:

$$C_R(x) = D_R(x)/P_R(x)$$

In step R3B of FIG. 1, the despiked sample spectrum, $D_S(x)$, is divided by the photometric standard spectrum measured on the sample channel to give a photometrically compensated sample spectrum:

$$C_S(x) = D_S(x)/P_S(x)$$

(3) Linearization

A spectrograph disperses radiation into its wavelength components such that, when projected onto a plane at the detector, the pixel position of a given wavelength component is, to a first order approximation, linearly related to its wavelength. However, the energy of the radiation is proportional to the reciprocal of its wavelength. Therefore, pixel position is a nonlinear function of energy, and the energy spacing between pixel positions is not constant. The number of pixels (data points) spanning a given energy interval in one part of a spectrum is different than that for an equal energy interval in a different part of the spectrum. Regions of different energies will effectively be weighted differently in a multivariate calibration that is built using spectra that have nonlinear energy dispersion bases. If the spectrometer were perfectly stable, the differences in effective weighing factors at different energies across a spectrum would not change and could be easily compensated for in the calibration technique. However, any instrument variabilities that create shifts in the energies of the Raman scattered radiation, e.g., shifts in the wavelength of the excitation laser, also create differences in the effective weighing factors across a measured spectrum, and these differences must be compensated in each individual spectrum. Although this compensation can be done directly, residual errors in the compensation process can be relatively large, resulting in large predictive errors in the calibration.

In the present invention, the weighting effects of the nonlinear energy dispersion of the spectrometer are effectively removed by transforming all measured spectra into equivalent spectra for which the relationship between pixel position and radiation energy is linear and for which the spectral data points are equally spaced in energy units. This transformation is referred to herein as linearization. A multivariate calibration built with linearized spectra will be weighted equally in all energy regions unless other weighting factors are purposely included. Compensation of spectral energy shifts in linearized spectra is significantly simpler than for nonlinearized spectra, and residual compensation errors are significantly lower, resulting in improved precision and accuracy of quantitative analyses.

Linearization is performed in two steps:

(i) calibration of the dispersion characteristics of the spectrometer, and (ii) interpolation of raw spectra to yield spectra that have data points equally spaced in energy units, the spacings being equal to those defined in the standard energy dispersion characteristic of the SURE.

(i) Calibration of spectrometer dispersion characteristics

The wavelength dispersion characteristics of a spectrometer can be defined in several different ways. The particular method used herein is to define the wavelength, $\lambda$, as a power series expansion in pixel position, x:

$$\lambda = a_0 + a_1 x + a_2 x^2 + a_3 x^3 + \ldots$$

To a very good approximation, this series may be truncated to the first two terms, yielding a linear expression relating wavelength and pixel position:

$$\lambda = a_0 + a_1 x$$

Calibration of the wavelength characteristics of spectrometers with array detectors has been extensively discussed in, for example, J. T. Brownrigg, "Wavelength Calibration Methods for Low-Resolution Photodiode Array Spectrometers" in *Appl. Spectrosc.*, 1993, vol. 47, pp1007–1014; M. Diem et al., "A Simple Algorithm to Convert Diode Array Spectral Data to Linear Wavelength or Wave Number Scales" in *Computer Enhanced Spectrosc.*, 1986, vol. 3, pp 29–33; M. Blanco et al., "Wavelength Calibration Transfer between Diode Array UV-Visible Spectrometers" in *Appl. Spectrosc.*, 1995, pp 593–597; D. A. Carter and J. E. Pemberton, "Frequency/Wavelength Calibration of Multipurpose Multichannel Raman Spectrometers. Part I: Instrumental Factors Affecting Precision," ibid., pp 1550–1560; D. A. Carter and J. E. Pemberton, "Frequency/Wavelength Calibration of Multipurpose Multichannel Raman Spectrometers. Part II: Calibration Fit Considerations," ibid.; pp 1561–1576; and J. Cho et al., "Wavelength Calibration Method for a CCD Detector and Multichannel Fiber-Optic Probes," ibid., pp 1841–1845, the disclosures of which are incorporated herein by reference.

Generally, calibration is accomplished by measuring spectra for standard reference materials that have spectral features at known wavelengths or at known Raman-shift energies, or both. The pixel positions measured for the known spectral features are then regressed against the known wavelengths (energies) to determine the coefficients of the calibration equation relating pixel position to wavelength (energy). In many spectroscopic applications, it is considered necessary to establish accurate values of the Raman-shift energies of all points in a spectrum. Such applications require that the absolute radiation energies, relative to the energy of the excitation source, be accurately known for each point in the spectrum. This requires standards that provide spectral features having well-known Raman-shift energies. Many such standards, which are usually organic chemical compounds, are known in the art.

For quantitative analytical applications using multivariate calibration methods, however, rigorous calibration of absolute Raman-shift energies is not required. A very accurate and precise calibration can be generated without knowing the absolute radiation energies of each point in the spectrum. A multivariate calibration determines the relationships between quantities or concentrations of sample components, as determined by some reference analytical method, and the shape of a measured spectrum, i.e., relative radiation intensities at each point in a spectrum. Neither the absolute values nor the dimensional units, e.g., pixel position, wavelength, or energy, of the dispersion basis need be known in order to obtain accurate quantitative predictions from the technique. The most important dispersion calibration criterion for multivariate quantitative analysis applications is that the dispersion basis be the same for each measured spectrum. Any standard reference material that provides reproducible calibrations of the dispersion basis is sufficient, even if it does not provide accurate absolute values of the Raman-shift energies for each point in the spectrum.

The standard reference material preferred in the present invention is an atomic emission source. An advantage of using an atomic emission source for calibration is that the radiation wavelengths of the atomic emission lines are well known and do not vary substantially with environmental conditions such as temperature and moisture. Furthermore, the radiation wavelengths and energies of atomic emission lines are constant; they do not depend upon the energy or wavelength of some external excitation source, as do the spectral features of chemical Raman-shift standards. Atomic emission lamps are also relatively inexpensive and are easily transported from one location to another.

The wavelength dispersion of the spectrometer is calibrated in steps M2A and M2B of FIG. 1 for the reference channel and sample channel, respectively, as follows: The spectrometer is illuminated at the sampling point with radiation from a standard atomic emission source, and spectra are recorded. Approximate pixel positions of the atomic emission lines are identified as the actual pixel positions corresponding to local maxima in the measured emission spectra that exceed a given intensity threshold. However, because the number of detector pixels and the resolution of the spectrometer are finite, it is possible that the true intensity maxima of the emission lines occur at positions lying between adjacent pixels. To obtain sufficient precision and accuracy in the determination of the dispersion coefficients, it is necessary to interpolate the measured spectra to locate the precise positions of the intensity maxima as a fraction of a pixel. This can be accomplished with any appropriate interpolation algorithm. In a preferred embodiment, it is accomplished by taking the first derivative of the acquired spectrum and interpolating the first derivative spectrum to determine more precise fractional pixel positions that correspond to zero-crossings. The set of more exact pixel positions are then regressed against the set of known wavelengths of the atomic emission lines to determine the values of the dispersion coefficients $a_0$ and $a_1$ in the calibration equation above. More precise and accurate values for the dispersion coefficients can be obtained by repeating this procedure many (typically a few hundred) times and averaging the many values obtained for both $a_0$ and $a_1$.

The dispersion coefficients $a_0$ and $a_1$ should not change unless the spectrometer changes in some way that alters its dispersion characteristics. Such changes can be expected to occur periodically under normal conditions found in most laboratory and process environments, and also whenever a major change is made to the spectrometer, for example, movement to a new location, replacement of an optical component affecting dispersion, etc. Steps M2A and M2B should therefore be repeated periodically as a maintenance procedure. The required frequency of recalibration will depend upon the analysis precision required for the application of interest and the environmental surroundings of the spectrometer.

(ii) Interpolation of raw spectra

The standard energy dispersion characteristic defined for the SURE specifies the number of points and the radiation energies corresponding to each point in a standard spectrum. In general, however, the dispersion properties of an actual spectrometer will differ from those defined for a standard spectrum. However, once the values of the dispersion coefficients $a_0$ and $a_1$ have been determined for a given spectrometer, every spectrum measured with that spectrometer can be transformed into an equivalent spectrum having the same number of points and the same energy spacing between points as those defined for the SURE. This transformation, denoted as $T_L[\ ]$, is applied in steps R4A and R4B of FIG. 1 to the reference spectrum and sample spectrum, respectively, to yield linearized reference and sample spectra:

$L_R(v) = T_L[C_R(x)]$ and $L_S(v) = T_L[C_S(x)]$

The transformation is accomplished as follows:

The absolute radiation energy corresponding to each point in a measured spectrum is calculated from its measured pixel position and the dispersion coefficients as $$E = \frac{hc}{\lambda} = \frac{hc}{a_0 + a_1 x}$$

where h is Planck's constant, c is the speed of light, $\lambda$ is the wavelength of radiation corresponding to each point, and x is the pixel position corresponding to each point. The energy units used for this calculation are chosen to be the same as those used to define the standard energy dispersion characteristic of the SURE. For example, if the standard energy dispersion characteristic were defined for absolute radiation energies in units of wavenumbers ($cm^{-1}$), and the dispersion coefficients for the spectrometer were determined for wavelengths in units of nanometers, the energy corresponding to each point in a measured spectrum is calculated as $$E(cm^{-1}) = \frac{10^7}{\lambda(nm)} = \frac{10^7}{a_0 + a_1 x}.$$

Alternatively, if the SURE dispersion characteristic is defined in terms of Raman-shift energy in units of $cm^{-1}$, and the dispersion coefficients for the spectrometer are determined for wavelengths (in units of nm), then the energy of each point in a measured spectrum is calculated as $$E(cm^{-1}) = E_{ex}(cm^{-1}) - \frac{10^7}{a_0 + a_1 x},$$

where $E_{ex}$ is the nominal radiation energy of the excitation source. It does not matter that the nominal energy of the radiation source may not equal the exact energy of the radiation source during the measurement of the spectra. It is only important that the energy calculated for each point in the spectrum relative to that of all other points in the spectrum be absolute and that the energy scale be the same as that defined for the standard energy dispersion characteristic of the SURE. An absolute value of energy is calculated for each point simply to facilitate the calculation of relative energies and to provide a well-defined energy scale for the interpolation process discussed below.

Once the relative energies for all points in a measured spectrum are known, the relationship between the measured radiation intensities and the relative radiation energies is determined by fitting the spectrum to a desired function that is subsequently used to predict the radiation intensities expected at the energies specified by the SURE standard energy dispersion characteristic.

Any desired function that provides the accuracy and precision required for a given application can be used in the interpolation process. The preferred embodiment of the present invention uses a cubic-spline interpolation algorithm to interpolate a measured spectrum to determine the radiation intensities expected at the energies specified by the SURE standard energy dispersion characteristic. Cubic-spline algorithms are described in, for example, W. H. Press et al., *Numerical Recipes: The Art of Scientific Computing*, 1986, Cambridge University Press, pp 86–89, the disclosure of which is incorporated herein by reference. By definition, the spectrum produced by this interpolation procedure has the same energy dispersion characteristic, i.e., the same number of points corresponding to the same energies, as that defined for the SURE.

It should be emphasized that although the energies corresponding to points in a linearized spectrum have been specified in the above process to be equal to those defined for the SURE, they may not actually equal the Raman-shift energies that were measured. The purpose of the linearization process is simply to transform all measured spectra into equivalent spectra that all have the same number of points with the same constant energy spacing between points. Linearization facilitates the dynamic standardization process and improves the accuracy and precision of quantitative analyses derived from standardized spectra.

(4) Optional Background Correction of Reference Spectrum

Step R5 in FIG. 1 is used to correct the reference spectrum, if desired, to remove undesired spectral features that are not directly related to the Raman signal of interest. For example, if diamond is used as a reference material, its Raman spectrum may contain a slight fluorescence background due to color impurities in the gem. Different diamonds may exhibit slightly different fluorescence levels, whereas their Raman peaks are all nearly identical. In such cases, it is desirable to remove the unwanted fluorescence signal from the spectrum but retain the peak arising from Raman scattering. This can be accomplished by any method that removes the undesired spectral features while retaining the shape of the Raman feature of interest. For example, a corrected spectrum may be generated by assigning a value of zero intensity to all data points that lie outside of a specified energy range that spans the Raman feature of interest while subtracting a baseline intensity from the original intensity values for all data points that lie within that energy range. The background correction operation, denoted herein as $T_B[\ ]$, is applied to the linearized reference spectrum to give the corrected reference spectrum:

$$B_R(v) = T_B[L_R(v)]$$

(5) Dynamic Standardization

The dynamic standardization process described in the previously discussed U.S. Pat. Nos. 5,455,673, 5,638,172, and 5,652,653 compensates for variabilities in the wavelength and/or intensity of the excitation source radiation; it can also compensate for minor mechanical positioning instabilities of the detector and optical dispersion element within a given spectrometer.

Dynamic standardization is accomplished by:

(a) determining the convolution function describing the spectral variations between the optionally corrected linearized reference spectrum and the previously defined standard reference spectrum, step R6 in FIG. 1, and (b) applying the convolution function to the linearized sample spectrum to produce a deconvoluted sample spectrum, step R7 in FIG. 1.

The convolution function describing spectral variations between the measured reference spectrum and the standard reference spectrum can be determined in a number of different ways, for example by iterative computation, which, however, is extremely tedious and time-consuming. A preferred method is to perform a Fourier transformation on both the optionally corrected linearized reference spectrum, $B_R(v)$, and the standard reference spectrum, $S_R(v)$, using a Fourier-transform (FT) algorithm as described, for example, in the previously mentioned text by Press et al., pp 381–383 and pp 407–412, the disclosures of which are incorporated herein by reference. The convolution function, $f(z)$, is then determined by dividing the FT of the measured spectrum by the FT of the standard spectrum:

$$f(z) = B_R'(z)[/]S_R'(z),$$

where a prime (') denotes the FT of a function and [/] represents complex division which accounts for both the real and imaginary components of the FT. The calculated convolution function, $f(z)$, contains the necessary information needed to compensate for instrumental variations and instabilities occurring during the acquisition of the sample spectrum. The FT of the sample spectrum, $L_S'(v)$, is then divided by $f(z)$, again using complex division, and the inverse FT of the result is calculated to give a deconvoluted sample spectrum, $S_D(v)$:

$$S_D(v) = FT^{-1}\{L_S'(z)[/]f(z)\}$$

where $FT^{-1}$ denotes the inverse Fourier transformation operation.

Although the dynamic standardization process itself is very successful in compensating for several variabilities and providing short-term standardization of a single Raman spectrometer, as demonstrated in U.S. Pat. Nos. 5,455,673, 5,638,172, and 5,652,653, it does not provide compensation for instrument-to-instrument variabilities or changes in the instrument response function. If dynamic standardization is applied directly to the measured spectra, a deconvoluted spectrum from one spectrometer may not represent the same energies and relative intensities as a deconvoluted spectrum from another spectrometer, due to variations in photometric response functions and dispersion characteristics between the instruments.

However, improved accuracy and precision of quantitative analyses can be obtained, and a robust and transferable calibration can be generated, if dynamic standardization is applied to spectra that have first been photometrically compensated and linearized by the methods described above. If the standard functions defined for the SURE are used to apply photometric compensation, linearization, and dynamic standardization on all spectrometers, then variabilities in the energies an and relative intensities of standard spectra from different spectrometers are greatly reduced.

(6) Weighting of Standard Spectra

In step R8 of FIG. 1, the deconvoluted sample spectrum, $S_D(v)$, is multiplied by the standard photometric response function defined for the SURE, $S_P(v)$, to give the standard sample spectrum, $S_S(v)$:

$$S_S(v) = S_D(v) \cdot S_P(v)$$

In some applications it may be desired to weight some regions of a spectrum more heavily than others when building a multivariate calibration. For those applications, the standard photometric response function can be defined so that those regions of the spectrum are multiplied by a larger factor than other regions of the spectrum. In cases where selective weighting of the spectrum is not desired, the standard photometric response function is defined to be independent of energy and equal to unity at all energies. In that case, the standard sample spectrum is equal to the deconvoluted sample spectrum resulting from step R7, i.e., step R8 has no effect on the spectrum.

All standard spectra generated by the transformations described above have been compensated for instrumental variabilities so that they appear as though they were obtained on the same spectrometer operating in the same standard state as that defined for the SURE. A multivariate calibration built using standard spectra can therefore be used to predict quantitative analyses from any other standard spectra that have been transformed to the SURE, independent of the particular spectrometer with which the spectra were acquired.

(7) Development of Normalized Calibration

In many cases, factors other than instrumental variabilities can affect measured spectra in a way that the transformations described above cannot compensate. For example, in molten or liquid process streams, interfering systematic or random effects such as bubbles, particulates, and turbidity can alter the overall intensity of the scattered radiation in an unpredictable fashion. Similarly, for solid samples, the sample shape, uniformity, and thickness can effect the overall intensity of the observed signal. When Raman spectra are obtained in a multiplexed fashion, i.e., the signal responses at all wavelengths are measured simultaneously, the effect of such interferences is to multiply an entire spectrum by an unknown constant that is unique to that individually collected spectrum. Spectral responses that have been multiplied by an unknown random number are not suitable for calibration directly using the usual multivariate statistical approaches that are known in the art.

As previously noted, U.S. Pat. No. 5,610,836 describes a method for building calibrations using spectra that are not normalized to the same intensity scales. In step C1 of FIG. 1, standard spectra obtained for a set of samples with known compositions or properties are used to generate a normalized calibration according to the method of this reference. Once generated, the normalized calibration is applied to a standard spectrum of an unknown sample, step R9 of FIG.1, to predict the composition or property of the unknown sample.

The following example further illustrates the invention:

EXAMPLE

Quantitative Analysis of Xylene Mixtures

The technical capability of the method of the present invention to standardize Raman spectrometers such that robust and stable calibration techniques relating Raman spectral responses to quantitative analyses of samples or processes can be generated, maintained, and transferred to any similar spectrometer was demonstrated by analyzing a sample set of 17 chemical mixtures comprising varying concentrations of para-, meta-, and ortho-xylene. The samples were prepared by carefully weighing varying amounts of each component into the mixture. The mole percent concentration of each component was calculated from the measured weights (see TABLE 1). Two Raman spectrometers, referred to below as SPEC1 and SPEC2, were used to perform quantitative analyses of the mixtures. Each spectrometer was constructed to contain a 700 mW multimode diode laser generating radiation near 797 nm that was pigtailed to a 100-$\mu$m silica quartz core, fiber optic cable (Spectra Diode Lab, Inc. San Jose, Calif., model number SDL-2372-P3). The incident radiation was split into two beams with a fiber optic beam splitter (Oz Optics Ltd., Carp, Ontario, Canada, model number FOBS-12-555-MMM-750-50/50). Each beam was focused onto a 200-$\mu$m core, polyimide-buffered, quartz silica fiber optic cable (Fiberguide Industries, Stirling, N.J.). The two fiber optic cables transmitted the radiation to both a sample probe and a reference probe.

The radiation in each fiber optic cable was filtered prior to entering the individual probes. The filters were designed to transmit only a narrow wavelength range near 800 nm (Omega Optical, Brattleboro, V.t., model number 800 BP10) and were inserted into fixed fiber optic filter holding devices (Oz Optics, Ltd., model number ND-200-55-750-M-30).

Both the reference and the sample fiber optic probes were constructed in-house using the method described in Buchanan et al., U.S. application Ser. No. 08/450,597, ROBUST SPECTROSCOPIC OPTICAL PROBE, filed May 25, 1995, now U.S. Pat. No. 5,657,404, the disclosure of which is incorporated herein by reference. The reference probe was used to illuminate a small diamond fragment. The sample probe was inserted into a 316 stainless steel sample tube in which the mixed xylene samples were placed.

Scattered radiation from both the reference and the sample was collected by individual 200-$\mu$m fibers positioned closely about the excitation fibers in the probes. The collected scattered radiation was filtered to remove nearly all of the Rayleigh scattered laser radiation prior to entering the return fiber. Each filter (Omega Optical, model number 800 REFLP) was held in a fixed fiber optic filter holding device (Oz Optics, Ltd., model number ND-200-55-750-M-30).

Both return fibers were directed back towards an Acton SpectraPro Spectrograph (Acton Research Corporation, Acton, Mass.), utilizing a 300 grooves/mm grating blazed at 750 nm. The grating on SPEC1 was centered at a wavelength of 901 nm. The grating of SPEC2 was centered at 899 nm. The two spectrographs were purposefully centered at different wavelengths to emphasize the success of the present standardization method.

A fiber adapter fashioned with eight 200-$\mu$m fiber inputs was connected at the entrance of each spectrograph to enable up to eight Raman signals to be acquired simultaneously on each instrument. The fibers were arranged into a linear array and positioned directly in front of the entrance slit of the spectrograph. One of these eight fibers was connected to the reference probe and another was connected to the sample probe. The dispersed radiation from the monochromator was detected by a thermoelectrically cooled CCD detector (Princeton Instruments, Trenton, N.J., model number TEA/CCD-512-TKM/2) and converted into an electronic signal. The CCD chip was a Techtronix 512×512 pixel, back-illuminated detector. The instrument was controlled using the ST130 Software Utilities provided by Princeton Instruments, incorporated into a software suite developed in-house for performing the necessary data acquisition and transformation algorithms.

An atomic emission lamp containing argon gas (Oriel, model number AR-6030) was used to calibrate the dispersion characteristics of each channel of each spectrometer, using seven emission lines with known wavelengths at 826.4522 nm, 840.821 nm, 842.4648 nm, 852.1442 nm, 912.2967 nm, 922.4499 nm, and 965.7786 nm.

A proprietary near-infrared fluorescent dye was used as a photometric standard. A dilute solution of the dye was placed into a stainless steel sample tube equipped to accommodate either the sample or reference optical probe. The photometric response functions of the reference and sample channels of each instrument were measured by immersing the corresponding probe into the dye solution and measuring a fluorescence spectrum on each channel, using the diode laser as a fluorescence excitation source.

For the xylene mixture application, the standard state of the SURE was defined as follows:

(a) Standard energy dispersion characteristic: Each standard spectrum comprised 800 data points equally spaced by 2 $cm^{-1}$ in Raman-shift energy units, spanning an energy range from 352 $cm^{-1}$ to 1950 $cm^{-1}$.

(b) Standard reference spectrum: A diamond fragment was used as the reference material for these measurements. The standard reference spectrum was obtained by measuring several spectra of the diamond reference on SPEC1 and averaging the results to obtain an average spectrum. The average spectrum was then linearized to transform it into the standard energy dispersion characteristic, using a cubic-spline interpolation algorithm as described in the previously mentioned text of Press et al. The reference spectrum was then background corrected to remove baseline noise and residual fluorescence signals by setting all points outside of a 60-point interval surrounding the maximum of the diamond Raman peak to zero intensity, and subtracting a baseline intensity from all points within that interval. The resulting spectrum was stored as the standard reference spectrum.

(c) Standard photometric response function: The standard photometric response function was defined as equal to unity at all Raman-shift energies.

Raman spectra were acquired on SPEC1 for eleven xylene mixtures (A–K in TABLE 1) that were used as a calibration sample set. Six different mixtures (L–Q in TABLE 1) served as an independent validation sample set. Raman spectra for the validation samples were acquired on both SPEC 1 and SPEC 2. Sample and reference spectra were simultaneously acquired for each sample in a random order, using a 30-second signal integration period.

Two calibrations were built to predict from measured Raman spectra the compositions, as mole percent of each of the three components, of the xylene mixtures. Control calibration, CAL1, was built using the unprocessed measured spectra as the multivariate signal response (matrix X). A calibration in accordance with the present invention, CAL2, was built using spectra that were transformed into standard spectra by the method of the invention, incorporating the normalization method described in previously discussed U.S. Pat. No. 5,610,836. A partial least squares (PLS) algorithm (UNSCRAMBLER, Computer Aided Modeling A.S., Trondheim, Norway) was used to build both calibrations. The known mole percent concentrations of the mixtures were used as the quantitative measurements (matrix Y) for both calibrations.

Using the 23 acquired spectra (11 calibration samples on SPEC1, 6 validation samples on SPEC1, and 6 validation samples on SPEC2), each calibration was applied to predict the compositions, as mole percent of each component, of the xylene mixtures. Control CAL1 was applied to spectra that had not been standardized. CAL2 of the invention was applied to spectra that were transformed into standard spectra.

The root-mean-square error of calibration (RMSEC) and the root-mean-square error of prediction (RMSEP) were calculated to estimate predictive capabilities of each calibration. The RMSEC was calculated for each mixture component as:

$$RMSEC(i) = \sqrt{\frac{\sum_{n=1}^{11}[p(i)-k(i)]^2}{11}}$$

where i=para-, meta-, or ortho-xylene, p(i) is the predicted mole percent value, k(i) is the known mole percent value, and the sum extends over the eleven samples of the calibration set.

The RMSEP for each mixture component was calculated for the validation sample set using spectra measured either on SPEC1 (RMSEP-SPEC1) or on SPEC2 (RMSEP-SPEC2):

$$RMSEP(i) = \sqrt{\frac{\sum_{n=1}^{6}[p(i)-k(i)]^2}{6}}$$

where the sum extends over the six samples of the validation set.

The results are summarized in TABLE 2. The average RMSEC for calibration CAL2 of the invention is approximately three times smaller than that for control calibration CAL1, and the average RMSEP-SPEC1 for CAL2 is nearly four times smaller than that for CAL1. These results demonstrate that the accuracy and precision of a calibration is significantly improved when it is generated using spectra that have been transformed to the SURE.

More importantly, the RMSEP-SPEC2 for CAL2 of the invention is consistently less than 0.15 mole percent for every mixture component, whereas RMSEP-SPEC2 for control CAL1 exceeds 3.5 mole percent for every component. For CAL2, the average RMSEP-SPEC2 is only slightly higher than the average RMSEP-SPEC1 (0.124 mole percent vs. 0.104 mole percent), even though the spectrograph grating of SPEC2 was purposefully set at a different wavelength than that for SPEC1. These results clearly demonstrate that a calibration generated using the process of the present invention can be successfully transferred to other instruments and used to provide accurate and precise quantitative analyses.

TABLE 1

Compositions of Mixed Xylene Samples

| | | Mole % | | |
|---|---|---|---|---|
| | Sample | Para-xylene | Meta-xylene | Ortho-oxylene |
| Calibration Set | A | 39.863 | 35.223 | 24.914 |
| | B | 39.984 | 25.011 | 35.005 |
| | C | 34.967 | 25.127 | 39.906 |
| | D | 34.779 | 39.929 | 25.292 |
| | E | 39.951 | 25.078 | 34.971 |
| | F | 33.343 | 33.323 | 33.334 |
| | G | 33.421 | 33.234 | 33.345 |
| | H | 25.12 | 39.943 | 34.937 |
| | I | 35.035 | 39.973 | 24.992 |
| | J | 39.97 | 35.01 | 25.02 |
| | K | 24.968 | 35.086 | 39.946 |
| Validation Set | L | 30.138 | 29.924 | 39.938 |
| | M | 30.031 | 39.903 | 30.066 |
| | N | 39.96 | 29.947 | 30.093 |
| | O | 35.006 | 35.03 | 29.965 |
| | P | 34.998 | 30.01 | 34.992 |
| | Q | 30.027 | 34.991 | 34.982 |

TABLE 2

Root-mean-square errors (Mole %) of calibration (RMSEC) and prediction (RMSEP) for xylene mixtures

| | CAL1 (Control) | | | CAL2 (Invention) | | |
|---|---|---|---|---|---|---|
| Calibration Technique: | Para- | Meta- | Ortho- | Para- | Meta- | Ortho- |
| RMSEC (Mole %): | 0.225 | 0.191 | 0.338 | 0.067 | 0.083 | 0.109 |
| RMSEP (Mole %), SPEC1: | 0.336 | 0.329 | 0.591 | 0.082 | 0.097 | 0.133 |
| RMSEP (Mole %), SPEC2: | 3.595 | 3.949 | 7.495 | 0.108 | 0.116 | 0.148 |

The invention has been described in detail with particular reference to preferred embodiments thereof, but it will be understood that variations and modifications can be effected within the spirit and scope of the invention.

What is claimed is:

1. A method for producing a standard Raman spectrum from a sample using a particular Raman spectrometry apparatus or any of a plurality of similar Raman spectrometry apparatus, each said Raman spectrometry apparatus comprising a substantially monochromatic radiation source, excitation optical means, reference optical collection means, at least one sample optical collection means, a spectrograph, and a multi-channel array detector, said method comprising:

(a) using said spectrometry apparatus, simultaneously irradiating a reference material and at least one sample;

(b) defining a standard energy dispersion characteristic, a standard Raman spectrum of said reference material, and a standard photometric response function;

(c) simultaneously acquiring at more than one wavelength a convolved Raman spectrum of said reference material using a reference channel of said multi-channel array detector and a convolved Raman spectrum of said sample using a sample channel of said multi-channel array detector, said convolved spectra comprising a Raman-shift energy region included within said standard energy dispersion characteristic;

(d) optionally identifying and removing noise spikes from each of the convolved Raman spectra of the reference material and the sample, thereby producing despiked convolved Raman spectra of said reference material and said sample;

(e) irradiating each optical collection means and the spectrograph using a second radiation source and detecting the resulting signals with said detector, thereby producing a corresponding photometric reference spectrum for each optical collection means;

(f) dividing each of the optionally despiked convolved Raman spectra of the reference material and the sample by said corresponding respective photometric reference spectrum, thereby producing compensated convolved Raman spectra of said reference material and said sample;

(g) irradiating the spectrograph using a third radiation source and detecting resulting signals in each channel of the multi-channel detector, thereby producing a corresponding third radiation source spectrum for each detector channel;

(h) from the corresponding third radiation source spectrum for each detector channel and said standard energy dispersion characteristic, constructing a corresponding wavelength,energy correlating equation for each detector channel;

(i) applying the corresponding wavelength/energy correlating equation for each detector channel to each corresponding compensated convolved Raman spectrum of the reference material and the sample, thereby producing linearized convolved Raman spectra of said reference material and said sample;

(j) optionally correcting the linearized convolved Raman spectrum of the reference material to remove background signals, thereby producing a corrected linearized convolved Raman spectrum of said reference material;

(k) determining a convolution function from the standard Raman spectrum of the reference material and the optionally corrected linearized convolved Raman spectrum of said reference material;

(l) applying the convolution function to adjust the linearized convolved Raman spectrum of the sample, thereby producing a deconvolved Raman spectrum of said sample; and (m) multiplying the deconvolved Raman spectrum of the sample by the standard photometric response function, thereby producing a standard Raman spectrum of said sample from a particular Raman spectrometry apparatus or from any of a plurality of similar Raman spectrometry apparatus.

2. The method according to claim 1 wherein said substantially monochromatic radiation source comprises a laser.

3. The method according to claim 2 wherein said laser is a multi-mode diode laser.

4. The method according to claim 1 wherein said convolved Raman spectrum of said sample includes said convolved Raman spectrum of said reference material.

5. The method according to claim 1 wherein said reference material comprises diamond.

6. The method according to claim 1 wherein said multi-channel array detector comprises a charge-coupled device.

7. The method according to claim 1 wherein said second radiation source includes fluorescent radiation obtained from a silicate glass doped with at least one metal oxide or from a solution of a fluorescent dye.

8. The method according to claim 1 wherein said second radiation source includes a white light emission source or a black body radiation source.

9. The method according to claim 1 wherein said third radiation source comprises an atomic emission source.

10. The method according to claim 9 wherein said atomic emission source is an argon lamp.

11. The method according to claim 1 wherein said third radiation source includes a material having a Raman spectrum with spectral features corresponding to known Raman-shift energies.

12. The method according to claim 1 wherein said applying the corresponding wavelength/energy correlating equation for each detector channel to each corresponding compensated convolved Raman spectrum of the reference material and the sample is carried out using a cubic-spline interpolation algorithm.

13. The method according to claim 1 wherein said defining the standard Raman spectrum of the reference material is carried out by adjusting a previously acquired convolved Raman spectrum of said reference material or by averaging a plurality of previously acquired Raman spectra of said reference material.

14. The method according to claim 1 wherein said determining the convolution function is carried out using a Fourier transform algorithm.

15. The method according to claim 1 wherein said standard energy dispersion characteristic comprises a plurality of spaced apart points, each of said points corresponding to a specified energy value.

16. The method according to claim 15 wherein each of said points is separated from adjacent points by a constant equal amount of energy.

17. The method according to claim 16 wherein said standard photometric response function comprises a weighting function, said weighting function being applied to said plurality of points comprising said standard energy dispersion characteristic.

18. The method according to claim 17 wherein said weighting function weights specified points of said plurality of points more heavily than other points.

19. The method according to claim 1 wherein each said corresponding photometric reference spectrum for each optical collection means is modulated along an intensity axis by the respective optical collection means, the spectrograph, and the detector.

20. The method according to claim 1 wherein each said corresponding third radiation source spectrum for each detector channel is modulated along a wavelength/energy dispersion axis by the spectrograph and the detector.

21. A method for providing an accurate and precise quantitative analysis of the chemical composition and/or physical properties of an unknown sample by generating a standardized calibration that can be applied to a particular Raman spectrometry apparatus or any of a plurality of similar Raman spectrometry apparatus, each said Raman spectrometry apparatus comprising a substantially monochromatic radiation source, excitation optical means, reference collection optical means, at least one sample collection optical means, a spectrograph, and a multi-channel array detector, said method comprising:

(a) using said spectrometry apparatus, simultaneously irradiating a reference material and at least one sample having a known chemical composition and/or known physical properties with said substantially monochromatic radiation source;

(b) defining a standard energy dispersion characteristic, a standard Raman spectrum of said reference material, and a standard photometric response function;

(c) simultaneously acquiring at more than one wavelength a convolved Raman spectrum of said reference material using a reference channel of said multi-channel array detector and a convolved Raman spectrum of said sample using a sample channel of said multi-channel array detector, said convolved spectra comprising a Raman-shift energy region included within said standard energy dispersion characteristic;

(d) optionally identifying and removing noise spikes from each of the convolved Raman spectra of the reference material and the sample, thereby producing despiked convolved Raman spectra of said reference material and said sample;

(e) irradiating each optical collection means and the spectrograph using a second radiation source and detecting the resulting signals with said detector, thereby producing a corresponding photometric reference spectrum for each optical collection means;

(f) dividing each of the optionally despiked convolved Raman spectra of the reference material and the sample by said corresponding respective photometric reference spectrum, thereby producing compensated convolved Raman spectra of said reference material and said sample;

(g) irradiating the spectrograph using a third radiation source and detecting resulting signals in each channel of the multi-channel detector, thereby producing a corresponding third radiation source spectrum for each detector channel;

(h) from the corresponding third radiation source spectrum for each detector channel and said standard energy dispersion characteristic, constructing a corresponding wavelength/energy correlating equation for each detector channel;

(i) applying the corresponding wavelength/energy-detector correlating equation for each detector channel to each corresponding compensated convolved Raman spectrum of the reference material and the sample, thereby producing linearized convolved Raman spectra of said reference material and said sample;

(j) optionally correcting the linearized convolved Raman spectrum of the reference material to remove background signals, thereby producing a corrected linearized convolved Raman spectrum of said reference material;

(k) determining a convolution function from the standard Raman spectrum of the reference material and the optionally corrected linearized convolved Raman spectrum of said reference material;

(l) applying the convolution function to adjust the linearized convolved Raman spectrum of the sample, thereby producing a deconvolved Raman spectrum of said sample; and (m) multiplying the deconvolved Raman spectrum of said sample by the standard photometric response function, thereby producing a standard Raman spectrum of said sample;

(n) repeating the process described in the preceding steps (a) through (m) using a plurality of samples of known chemical composition and/or physical properties, thereby producing a set of multivariate signal responses comprising standard Raman spectra of said samples;

(o) from the set of multivariate signal responses comprising standard Raman spectra for the samples and from the known chemical composition and/or physical properties of said samples, constructing a normalized calibration; and (p) applying the normalized calibration to a standard Raman spectrum obtained from a sample of unknown chemical composition and/or physical properties using said Raman spectrometry apparatus or any similar Raman spectrometry apparatus having substantially the same elements as said Raman spectrometry apparatus, thereby providing an accurate and precise quantitative analysis of the chemical composition and/or physical properties of said sample.

22. The method according to claim 21 wherein said substantially monochromatic radiation source comprises a laser.

23. The method according to claim 22 wherein said laser is a multi-mode diode laser.

24. The method according to claim 21 wherein said convolved Raman spectrum of said sample includes said convolved Raman spectrum of said reference material.

25. The method according to claim 21 wherein said reference material comprises diamond.

26. The method according to claim 21 wherein said multi-channel array detector comprises a charge-coupled device.

27. The method according to claim 21 wherein said second radiation source includes fluorescent radiation from a silicate glass doped with at least one metal oxide or from a solution of a fluorescent dye.

28. The method according to claim 21 wherein said second radiation source includes a white light emission source or a black body radiation source.

29. The method according to claim 21 wherein said third radiation source comprises an atomic emission source.

30. The method according to claim 29 wherein said atomic emission source is an argon lamp.

31. The method according to claim 21 wherein said third radiation source includes a material having a Raman spectrum with spectral features corresponding to known Raman-shift energies.

32. The method according to claim 21 wherein said applying the corresponding wavelength/energy correlating equation for each detector channel to each corresponding compensated convolved Raman spectrum of the reference material and the sample is carried out using a cubic-spline interpolation algorithm.

33. The method according to claim 21 wherein said defining the standard Raman spectrum of the reference material is carried out by adjusting a previously acquired convolved Raman spectrum of said reference material or by averaging a plurality of previously acquired convolved Raman spectra of said reference material.

34. The method according to claim 21 wherein said determining the convolution function is carried out using a Fourier transform algorithm.

35. The method according to claim 21 wherein said standard energy dispersion characteristic comprises a plurality of spaced apart points, each of said points corresponding to a specified energy value.

36. The method according to claim 35 wherein each point is separated from adjacent points by a constant equal amount of energy.

37. The method according to claim 36 wherein said standard photometric response function comprises a weighting function, said weighting function being applied to said plurality of points comprising said standard energy dispersion characteristic.

38. The method according to claim 37 wherein said weighting function weights specified points of said plurality of points more heavily than other points.

39. The method according to claim 21 wherein each said corresponding photometric reference spectrum for each optical collection means is modulated along an intensity axis by the respective optical collection means, the spectrograph, and the detector.

40. The method according to claim 21 wherein each said corresponding third radiation source spectrum for each detector channel is modulated along a wavelength/energy dispersion axis by the spectrograph and the detector.

41. The method according to claim 21 wherein said constructing the normalized calibration for said Raman spectrometry apparatus is carried out using principal factor analysis or a partial least squares algorithm.

42. The method according to claim 21 wherein said unknown sample comprises a polymeric composition.

43. The method according to claim 42 wherein said polymeric composition comprises a cellulosic composition.

44. The method according to claim 42 wherein said polymeric composition comprises a polymeric material produced by the reaction of lower molecular weight reactant compounds.

45. The method according to claim 44 wherein said polymeric material comprises a polyester.

46. The method according to claim 44 wherein said polymeric material comprises a polyolefin.

47. The method according to claim 21 wherein said unknown sample comprises material situated in a chemical reaction process stream.

48. The method according to claim 21 wherein said unknown sample comprises material situated in a distillation apparatus.

49. The method according to claim 21 wherein said unknown sample comprises material situated in a living organism.

* * * * *